United States Patent [19]
Thompson et al.

[11] Patent Number: 6,021,781
[45] Date of Patent: Feb. 8, 2000

[54] INTRAURETHRAL PRESSURE MONITORING ASSEMBLY AND METHOD OF TREATING INCONTINENCE USING SAME

[75] Inventors: Ronald J. Thompson, Ft. Thomas, Ky.; Jack B. Stubbs, Waynesville, Ohio

[73] Assignee: Medworks Corporation, Louisville, Ky.

[21] Appl. No.: 09/040,957

[22] Filed: Mar. 18, 1998

[51] Int. Cl.$^7$ ...................................................... A61B 19/00
[52] U.S. Cl. .............................................. 128/898; 600/29
[58] Field of Search ..................................... 600/485–488, 600/561, 587, 591, 29–31; 73/1.57, 1.66

[56] References Cited

U.S. PATENT DOCUMENTS

| | | |
|---|---|---|
| 1,666,332 | 4/1928 | Hirsch . |
| 3,911,902 | 10/1975 | Delpy . |
| 3,911,927 | 10/1975 | Rich et al. . |
| 4,063,548 | 12/1977 | Klatt et al. . |
| 4,072,144 | 2/1978 | Pelosi et al. . |
| 4,073,287 | 2/1978 | Bradley et al. . |
| 4,133,303 | 1/1979 | Patel . |
| 4,149,539 | 4/1979 | Cianci . |
| 4,191,196 | 3/1980 | Bradley et al. . |
| 4,356,610 | 11/1982 | Hon et al. . |

(List continued on next page.)

FOREIGN PATENT DOCUMENTS

| | | |
|---|---|---|
| WO9310715 | 6/1993 | WIPO . |
| WO9700047 | 1/1997 | WIPO . |

OTHER PUBLICATIONS

Buchsbaum & Schmidt *Gynecologic and Obstetric Urology*, W. B. Saunders Company, Third Editioin, 1993: Juma, Saad et al., *Evaluation of Stress Urinary Incontinence* (Chapter 15).

Juma, Saad et al., *Urodynamics* (Chapter 16) Dec. 1993.

Lee, Raymond A., *Modified Marshall–Marchetti–Krantz Operation in Primary and Recurrent Urinary Stress Incontinence* (Chapter 18) Dec. 1993.

Lebherz, Thomas B. et al., *The Modified Pereyra Procedure* (Chapter 19) Dec. 1993.

Nachtshiem, Daniel A. et al., *Transvaginal Urethropexy with Endoscopic Control* (Chapter 20) Dec. 1993.

Beck, R. P., *The Sling Operation* (Chapter 21) Dec. 1993.

Benderev, Theodore V., "A Modified Percutaneous Outpatient Bladder Neck Suspension System", *The Journal of Urology*, (Dec. 1994) vol. 152, pp. 2316–2320.

"Urinary Incontinence", *ACOG Technical Bulletin*, (Oct. 1995) No. 213, pp. 1–11.

Pelosi III, Marco A., et al., "Laparoscopic–Assisted Pubovaginal Sling Procedure for the Treatment of Stress", *The Journal of the American Associate of Gynecologic Laparoscopists*, (Aug. 1996) vol. 3, No. 4, pp. 593–600.

Kovak, S. Robert, et al., "Pubic bone suburethral stabilization sling: a long–term cure for SUI?", *Contemporary OB/GYN*, (Feb. 1998) pp. 52, 55–56, 59–60, 62,66, 72, 74,76.

(List continued on next page.)

*Primary Examiner*—Samuel Gilbert
*Attorney, Agent, or Firm*—Dinsmore & Shohl LLP

[57] ABSTRACT

A method of treating urinary incontinence in a patient by: providing a pressure monitor probe comprising a catheter having a pressure responsive region and a distal portion, the pressure responsive region spaced a predetermined distance from the distal portion; inserting the pressure monitor probe into the patient's urethra such that the distal portion is positioned in the patient's bladder adjacent the UVJ, thereby positioning the pressure responsive region of the catheter within the urethra a predetermined distance from the UVJ; and surgically modifying the pressure applied against the urethra while monitoring the pressure applied against the urethra using the probe. An intraurethral pressure monitor probe and an intraurethral pressure monitoring assembly are also provided.

27 Claims, 3 Drawing Sheets

U.S. PATENT DOCUMENTS

| | | |
|---|---|---|
| 4,407,301 | 10/1983 | Streisinger . |
| 4,538,621 | 9/1985 | Jarczyn .................................. 600/561 |
| 4,612,939 | 9/1986 | Robertson . |
| 4,660,560 | 4/1987 | Klein . |
| 4,727,887 | 3/1988 | Haber . |
| 4,757,194 | 7/1988 | Simms . |
| 4,776,347 | 10/1988 | Matthews . |
| 4,790,328 | 12/1988 | Young . |
| 4,809,710 | 3/1989 | Williamson . |
| 4,825,875 | 5/1989 | Ninan et al. . |
| 4,873,990 | 10/1989 | Holmes et al. ......................... 600/561 |
| 4,887,610 | 12/1989 | Mittal . |
| 4,938,760 | 7/1990 | Burton et al. . |
| 5,007,898 | 4/1991 | Rosenbluth et al. . |
| 5,013,292 | 5/1991 | Lemay ..................................... 600/30 |
| 5,019,032 | 5/1991 | Robertson . |
| 5,103,835 | 4/1992 | Yamada et al. . |
| 5,167,237 | 12/1992 | Rabin et al. . |
| 5,385,563 | 1/1995 | Gross . |
| 5,507,796 | 4/1996 | Hasson . |
| 5,517,998 | 5/1996 | Madison . |
| 5,546,935 | 8/1996 | Champeau . |
| 5,588,965 | 12/1996 | Burton et al. . |
| 5,591,163 | 1/1997 | Thompson . |
| 5,637,074 | 6/1997 | Andino et al. . |
| 5,637,091 | 6/1997 | Hakky et al. . |
| 5,643,288 | 7/1997 | Thompson . |
| 5,647,836 | 7/1997 | Blake, III et al. . |
| 5,657,764 | 8/1997 | Coulter et al. . |
| 5,662,654 | 9/1997 | Thompson . |
| 5,697,931 | 12/1997 | Thompson . |
| 5,836,314 | 11/1998 | Bendereve et al. . |
| 5,836,315 | 11/1998 | Benderev et al. ...................... 128/898 |

OTHER PUBLICATIONS

Raboy, Peter A., et al., "Extraperitoneal Endoscopic Vesicourethral Suspension (EEVUS)", *Current Surgical Techniques in Urology*, (1993) vol. 6, Issue 5, pp. 1–8.

Leach, Gary E., "Bone Fixation Technique For Transvaginal Needle Suspension", *Urology* (May 1988) vol. XXXI, No. 5, pp. 388–390.

Pelosi, Marco A., et al., "Laparoscopic Hysterecomy with Bilateral Salpingo–oophorectomy Using a Single Umbilical Puncture", *New Jersey Medicine* (Oct. 1991) vol. 88, No. 5, pp. 721–726.

Benderev, Theodore V., "Anchor Fixation and Other Modifications of Endoscopic Bladder Neck Suspension", *Urology*, (Nov. 1992), vol. 40, No. 5, pp. 409–418.

Nezhat, Ceana H., et al., "Laparoscopic Retropubic Cystourethropexy", *The Journal of the American Association of Gynecologic Laparoscopists*, (Aug. 1994) vol. 1, No. 4, Part 1, pp. 339–349.

Salerno, Robert L., "Using the laparoscope for SUI", *Contempory OB/GYN*, (Dec. 1994) pp. 35–40.

Liu, C.Y., "Laparoscopic Retropubic Colposuspension (Burch Procedure)" 12 pgs. (1993).

Krants, Kermit E., "The Marshall–Marchetti–Krantz Surgical Technique for Urinary Stress Incontinence", Mitek® Surgical Products, Inc. Brochure, 4 pgs. (1993).

"Retropubic Bladder Neck Suspension System", Mitek® Surgical Products, Inc. Brochure, 4 pgs. (1994).

Mascio, Valenzio C., "Retropubic periurethral bladder neck suspension using Mitek anchors", reprinted from *Contemporary OBGYN*, (Jul. 1996), 6 pgs.

INTRAURETHRAL PRESSURE MONITORING ASSEMBLY AND METHOD OF TREATING INCONTINENCE USING SAME

BACKGROUND OF THE INVENTION

1. Field of the Invention

The present invention is directed towards apparatus and methods for monitoring pressure within a patient's urethra. The present invention provides an intraurethral pressure monitor probe which may be used to monitor external pressure applied against the patient's urethra, particularly during a surgical procedure to correct urinary incontinence.

2. Description of Related Art

Female stress urinary incontinence ("SUI"), defined as the unintentional loss of urine, is a common problem after vaginal childbirth. In women afflicted with this problem, the incontinence usually occurs during coughing, sneezing, or physical activity. While effective surgical treatment for this condition has existed for many decades, the procedures typically involve major abdominal surgery with accompanying post-operative limitations lasting six to eight weeks. Because of the nature of some of the currently-employed surgical procedures and the risks associated therewith, many women simply resort to diaper-like incontinence pads, or simply avoid any activities which may result in the unintentional loss of urine.

Continence generally requires proper functioning of the bladder and the intrinsic sphincter muscle which surrounds the urethra, as well as the proper anatomical relationship between the bladder, the urethra and other abdominal structures. In the normal resting state, the closure force provided by the intrinsic sphincter, as well as external pressure exerted on the collapsible urethra by the surrounding musculature, both provide sufficient force to overcome bladder pressure, thereby maintaining continence. During moments of coughing, sneezing, or other physical activities, greater pressure will be exerted on the dome of a filled bladder. In women not afflicted with SUI, the increased intra-abdominal pressure is also transmitted to the urethra, and this increased external pressure on the urethra acts to prevent the unwanted loss of urine. Sufferers of SUI, however, are not so fortunate.

SUI is generally caused by two anatomic etiologies: intrinsic sphincter deficiency ("ISD"); and a loss of support of the periurethral tissue at the urethra-vesicular junction ("UVJ"—the region where the urethra enters the bladder). The latter situation (also known as hypermobile bladder neck) often occurs after vaginal childbirth, and is caused by the separation of the connective tissue which secures the periurethral tissue to the underside of the pubic bone. When this occurs, the UVJ will sag into the vagina, thereby reducing transmission of intra-abdominal pressure to the urethra during moments of stress (such as coughing or laughing). ISD, on the other hand, is a functional problem in that the urethral sphincter does not respond to sudden increases in intra-abdominal pressure. ISD can be caused by muscular withering with age, arterial sclerosis, diabetes, or prior incontinence surgery, all of which are related to a compromised blood supply to the detrusor muscle surrounding the urethra.

For both types of stress urinary incontinence, various types of surgical procedures have been developed which often provide relief. "Urethropexy" procedures suspend a portion of the tissue adjacent to the patient's urethra (also referred to as the periurethral tissue) relative to a structure within the patient's body by means of a fixation device (such as sutures). In one common procedure, the results of which are depicted in FIG. 3 herein, sutures are secured between the periurethral tissue on either side of the urethra and an anatomical structure located above the urethra. Typically, the sutures are secured between the periurethral tissue and the pubic bone (either using bone anchors or by suturing directly to the periosteum of the pubic bone), Cooper's ligament, or the abdominal fascia. The sutures pull the vaginal wall and periurethral tissue upwardly towards the urethra, which in turn provides an upward force on the urethra (indicated by the arrows in FIG. 3). This upward force acts to restore the urethra to the desired elevation or angle, thereby allowing increases in intra-abdominal pressure to be transmitted to the urethra (as an external force). Such procedures are described, for example, in U.S. Pat. Nos. 5,591,163, 5,643,288, 5,662,654 and 5,697,931, all of which are incorporated herein by reference.

Another type of urethropexy procedure often employed is referred to as a "sling procedure." A sling procedure is particularly recommended when the incontinence is caused by ISD or when the support tissues at the bladder neck (i.e., UVJ) are irreparably damaged. In the sling procedure (also known as a pubovaginal or suburethral sling procedure), a strip of flexible material (i.e., the sling) is positioned beneath the urethra, and its two ends are suspended from an anatomical support structure. Typically, the width of the sling is such that it extends from the UVJ to at least the midpoint of the urethra. As seen in FIG. 2 herein, the sling is employed to both lift and support the urethra in order to provide continence. The urethra is elevated and is supported underneath by the sling. The sling also applies an upward closure pressure on the urethra, thereby alleviating any portion of the incontinence caused by intrinsic sphincter deficiency. The sling may be attached either directly to a supporting structure, (such as the abdominal fascia) or by means of another fixation device such as one or more sutures. Typically, the sling is sutured to the pubic bone (either by way of bone anchors or suturing directly to the periosteum), Cooper's ligament or abdominal fascia. An exemplary sling procedure, as well as apparatus for use in such procedure, is described in further detail in application Ser. No. 08/818, 391, filed on Mar. 14, 1997, pending which is incorporated herein by reference.

In the sling procedure, the sling itself must be positioned beneath the urethra such that it can be employed to provide an upward force to elevate the urethra. Therefore, the sling must be positioned beneath the vaginal mucosa, typically so that it is located between the vaginal mucosa (i.e., the vaginal wall) and the periurethral fascia located directly beneath the urethra. This generally requires that the surgeon create a vaginal skin flap by peeling a portion of the vaginal mucosa away from the fascia located beneath the urethra (also referred to as the pubocervical fascia).

In either of the above-described procedures for treating incontinence by elevating the patient's urethra, the upper force provided by the fixation device (e.g., the sutures or the sling) must be sufficient to provide continence, while not being so great that the patient is unable to urinate. Thus, the surgeon would prefer a method of determining the amount of pressure applied against the urethra while the procedure is being performed, thereby ensuring that the sutures (FIG. 3) or sling (FIG. 2) provide the proper upward force. It must be kept in mind, however, that the force provided by the existing structures within the patient, including the intrinsic sphincter, must be taken into account. For example, if the patient suffers from hypermobile bladder neck as well as intrinsic sphincter deficiency, the degree of elevation which will correspond to the pressure imparted by the sling will need to be greater than if the patient only suffers from hypermobile bladder neck. Therefore, there is a need for a pressure monitoring device which will monitor intraurethral pressures while the incontinence procedure is being performed. As used herein, the term "intraurethral pressure" simply refers to the external pressure applied against the urethra, and includes the force imparted by the intrinsic sphincter, as well as the tissue and musculature surrounding the urethra. The pressure monitoring device should also be configured so as to isolate the urethra from the bladder, thereby ensuring that internal bladder pressure does not influence the pressure reading obtained.

Although numerous types of pressure monitoring devices have been developed for measuring pressures within body cavities, including the urethra, none of these prior art apparatus can be effectively employed during a surgical procedure to correct incontinence. Two of the more significant drawbacks associated with existing pressure monitoring devices is that most do not provide an effective means of eliminating the influence of bladder pressure. In addition, it is often difficult, if not impossible, to ensure that the pressure responsive region of the monitor is positioned at the proper location within the urethra. This is particularly problematic when the pressure monitor is positioned within the urethra while the procedure is being performed. As the urethra is elevated by means of the sutures and/or the sling, pressure monitoring devices of the prior art will not remain in the proper location within the urethra. Furthermore, any type of rigid probe extending through the entire length of the urethra will also interfere with proper restoration of the urethral angle. Therefore, there is a need for an intraurethral pressure monitor probe which overcomes these deficiencies of the prior art.

BRIEF DESCRIPTION OF THE DRAWINGS

While the specification concludes with claims particularly pointing out and distinctly claiming applicants' invention, it is believed that the same will be better understood from the following description taken in conjunction with the accompanying drawings in which:

Figure 1:
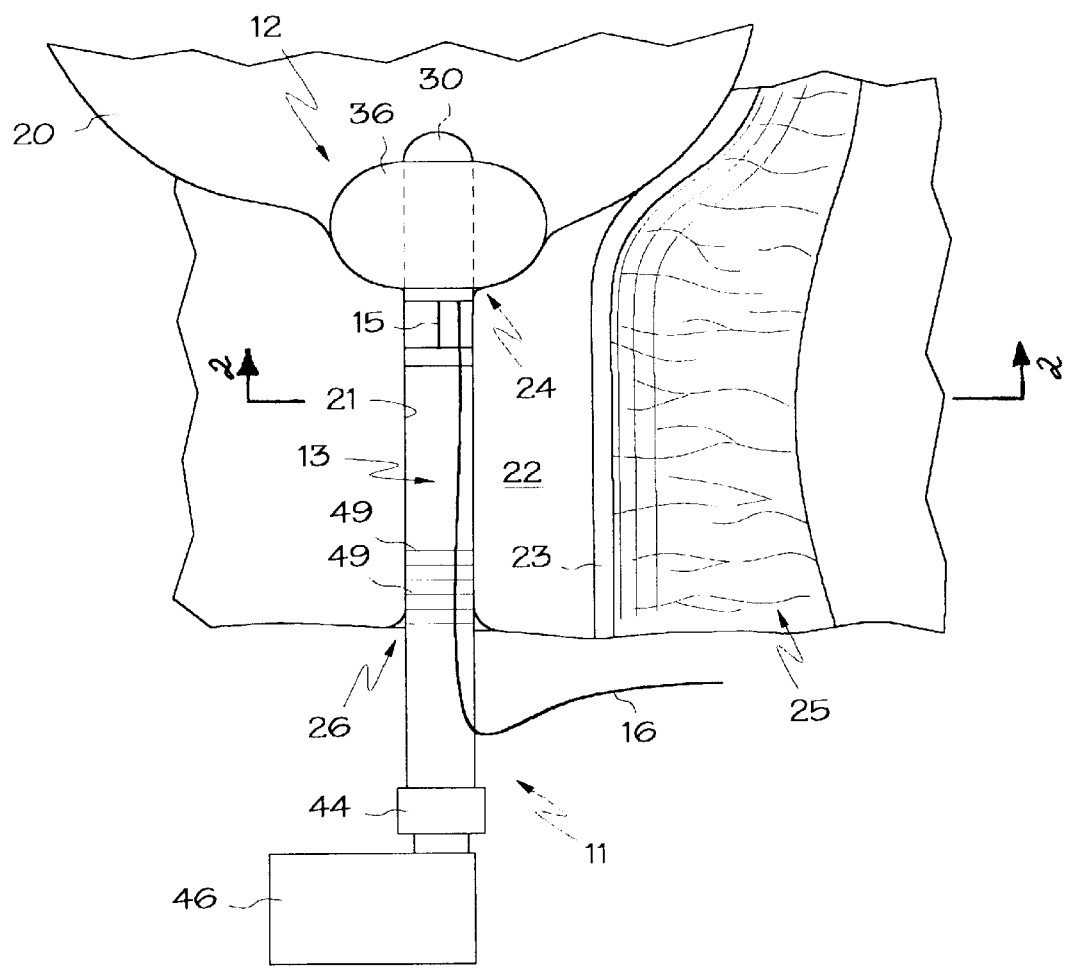
FIG. 1 is a cross-sectional view taken adjacent the midline of a patient, wherein the pressure monitor probe of the present invention has been positioned within a patient's urethra and bladder.

SUMMARY OF THE PREFERRED EMBODIMENTS,

It is an object of the present invention to provide apparatus and methods for monitoring pressure within a patient's urethra.

It is another object of the present invention to provide apparatus and methods for monitoring the external pressure applied against a patient's urethra, particular during a surgical procedure to correct incontinence.

It is yet another object of the present invention to provide a pressure monitor probe which may be secured in a patient's urethra a predetermined distance from the UVJ.

The foregoing objects, and others not specifically enumerated above, may be accomplished, in accordance with one preferred embodiment of the present invention, by providing a method of treating urinary incontinence in a patient, comprising:

(a) providing a pressure monitor probe, the probe comprising a catheter having a pressure responsive region and a distal portion, the pressure responsive region spaced a predetermined distance from the distal portion;

(b) inserting the pressure monitoring probe into the patient's urethra such that the distal portion is positioned within the patient's bladder (partially or completely within the bladder) adjacent the patient's UVJ (i.e., at or adjacent to the UVJ), thereby positioning the pressure responsive region of the catheter within the urethra a predetermined distance from the UVJ; and (c) surgically modifying the pressure applied against the urethra while monitoring the pressure applied against the urethra using the probe. The step of surgically modifying the pressure applied against the urethra may comprise elevating the patient's urethra, particularly by suspending a portion of the tissue adjacent the patient's urethra from an anatomical structure within the patient's body using a fixation device. The fixation device may comprise, for example, sutures extending between the periurethral tissue and an anatomical structure above the urethra (including the pubic bone, Cooper's ligament, or the abdominal fascia). Alternatively, a suburethral sling may be used as the fixation device, and this sling may be suspended directly from the anatomical structure, or may even be suspended by means of sutures or other similar well-known devices. The step of surgically modifying the pressure applied against the urethra may also comprise injecting a bulking agent, such as collagen, adjacent to the patient's urethra. The collagen acts to close off the urethra, similar to the manner in which the intrinsic sphincter closes off the urethra, and therefore the amount of collagen needed can be determined by monitoring intraurethral pressure using the probe of the present invention.

In the above methods, the interior of the catheter at the pressure responsive region should be isolated from the distal portion, and the distal portion should be positioned within the patient's bladder adjacent the UVJ. The distal portion is configured such that it prevents fluid communication between the bladder and the interior of the urethra, and also may be anchored in the bladder adjacent the UVJ. The catheter preferably comprises an elongate, deformable tube, having distal and proximal ends. A pressure monitor may be attached to the proximal end of the catheter, the pressure monitor configured so as to provide an indication of pressure applied to the exterior of the catheter, which in turn corresponds to the external pressure on the urethra. The catheter is also preferably hollow, and includes therein a fluid (preferably air), such that the pressure monitor will be responsive to the fluid pressure within the catheter.

The above methods also preferably include the step of anchoring the distal portion within the patient's bladder. The distal portion may be inflatable such that the step of anchoring the distal portion within the bladder comprises inflating the distal portion, and thereafter applying countertraction to the probe such that the distal portion will be held within the bladder adjacent to (more preferably directly against) the UVJ. The distal portion may comprise a hollow member having an aperture, and an inflatable portion positioned such that the aperture provides fluid communication between the interior of the hollow member and the inflatable portion. The inflation step may therefore comprise injecting a fluid into the interior of the hollow member so that the fluid (preferably air or saline) is expelled through the aperture to inflate the inflatable portion. A fluid source may also be provided, and can be attached to the distal portion such that the fluid source is in fluid communication with the interior of the hollow member. Fluid is thereafter expelled from the fluid source into the interior of the hollow member, thereby inflating the balloon. This fluid source may comprise, for example, a syringe having a needle attached thereto, and the needle may be attached to the distal portion by urging the tip of the needle into the interior of the distal portion.

An intraurethral pressure monitor probe is also provided, the probe comprising:

(a) a catheter having a pressure responsive region; and (a) a distal portion spaced away from the pressure responsive region and configured such that the distal portion may be anchored within a patient's bladder; wherein the probe is configured such when the distal portion is positioned within a patient's bladder adjacent the UVJ and anchored in the bladder, the pressure responsive region of the catheter will be located in the urethra a predetermined distance from the UVJ. The distal end of the catheter is preferably attached to the distal portion of the probe by a flexible, non-stretchable connector, such as a filament (more preferably a string). The distal portion may include an inflatable balloon portion, as described above, and also may include a deflation channel for selectively deflating the balloon. While various types of balloons may be used, the balloon preferably comprises a polymeric tube which extends about, and is sealed to, the circumference of the hollow member.

Finally, a packaged intraurethral pressure monitoring assembly is also provided, and comprises:

(a) an elongate pressure monitor probe;

(b) a rigid shaft extending parallel and adjacent to the probe; and (c) a polymeric film enclosing at least a portion of the probe and the shaft; the assembly configured such that at least a portion of the probe and the shaft may be inserted into a patient's urethra in order to monitor the pressure applied against the urethra. The rigid shaft may comprise the inflation needle described above. The film is preferably secured to the shaft and has a weakened region configured such that when the shaft is pulled away from the probe, the film will separate at the weakened region and will be pulled away from the probe along with the shaft, thereby exposing the probe. The pressure monitor may also be enclosed within the film.

DETAILED DESCRIPTION OF THE INVENTION

The present invention provides a pressure monitor probe which can be used in conjunction with standard pressure sensors (or gauges) in order to monitor intraurethral pressure, particularly during a surgical procedure to correct incontinence. The pressure monitor probe may be positioned within the patient's urethra in order to monitor the external forces applied against the urethra, including pressure from the intrinsic sphincter and pressure resulting from the elevation of the urethra by means of a fixation device. The pressure monitor probe of the present invention has a pressure responsive region which may be precisely positioned within a patient's urethra at the desired, predetermined location. The pressure monitor probe of the present invention has a distal portion which may be anchored within the bladder adjacent the UVJ, thereby ensuring that the pressure responsive region remains in the desired location within the urethra even while the urethra is being elevated in order to correct incontinence or while a bulking agent such as collagen is injected about the urethra.

FIG. 1 is a cross-sectional view taken adjacent the midline of a patient, wherein pressure monitor probe 11 of the present invention has been positioned within urethra 21 and bladder 20. For purposes of describing the method's of using the apparatus of the present invention, the patient's periurethral tissue is defined at 22 (primarily fascia), and the vaginal wall (or vaginal mucosa) is defined at 23. The region where urethra 21 meets bladder 20 is defined as the urethralvesicular junction ("UVJ") 24, and the exterior entrance to the urethra, defined at 26, is located immediately above vaginal canal 25.

Pressure monitor probe 11 has a distal portion 12 and a catheter 13 attached thereto. Distal portion 12 and catheter 13 are preferably attached to one another such that the interior of catheter 13 is isolated from distal portion 12. In addition, they should be attached to one another such that the region between distal portion 12 and the distal end of catheter 13 is flexible so as to allow catheter 13 to move relative to distal portion 12. This region of flexibility should also be isolated from the interior of catheter 13 such that movement of catheter 13 relative to distal portion 12 will not influence the pressure reading obtained from the probe. The incontinence procedures described previously will generally result in the urethra being pivoted upwardly from the UVJ. Therefore, the region where distal portion 12 is connected to catheter 13 should also be flexible enough so that it will not interfere with the upward pivoting of the urethra (i.e., the elevation of the urethra) during such procedures.

Catheter 13 and distal portion 12 may be attached to one another by any of a variety of connectors. It is preferred that the connector be non-stretchable so that the distance between catheter 13 and distal portion 12 cannot exceed a prescribed limit. In one preferred embodiment, a nonstretchable, yet flexible, filament 15 is employed for this purpose. Filament 15 may comprise a string, a thread, a wire, or other similar filaments. A preferred filament is a Gortex® thread, due to the fact that such material is flexible but will not stretch. Other types of connectors may also be employed for attaching distal portion 12 to catheter 13. It is preferred that the length of this connector, such as filament 15, be selected such that pressure responsive region 40 (to be described) is positioned a predetermined distance from the UVJ, more preferably between about 0.2 and about 0.3 cm from the UVJ.

Pressure monitor probe 11 is configured for insertion into the patient's urethra through urethral entrance 26, towards bladder 20. When properly inserted, distal portion 12 will be positioned within bladder 20 adjacent UVJ 24, as shown. The principal purpose of distal portion 12 is to anchor the probe at the precise, desired location. Therefore, distal portion 12 is configured such that it may be anchored at a location adjacent to UVJ 24 (adjacent meaning at or in close proximity to the UVJ). While various configurations may be employed for distal portion 12, in a preferred embodiment, distal portion 12 is expandable such that after it is inserted into the bladder distal portion 12 may be expanded so as to prevent removal therefrom. Once distal portion 12 is within bladder 20, it is expanded and catheter is 13 pulled outwardly in order to seat distal portion 12 at UVJ 24, as shown in FIG. 1. Countertraction on the probe (i.e., pulling the probe away from the bladder) will anchor distal portion 12 in place, although it will be recognized that the countertraction should be maintained in order to ensure that distal portion 12 remains anchored in the desired location. Of course it is also possible that distal portion 12 may be configured such that countertraction is not needed to anchor distal portion 12 in place, the preferred embodiments of the present invention ensure that the anchoring process (including countertraction) will not damage the bladder or urethra. Although the expandable feature of distal portion 12 may be provided by any of a number of structures, such as mechanically extending (or expanding) members and the like, distal portion 12 is preferably inflatable. In this manner, distal portion 12 is similar to a Foley catheter.

Figure 4:
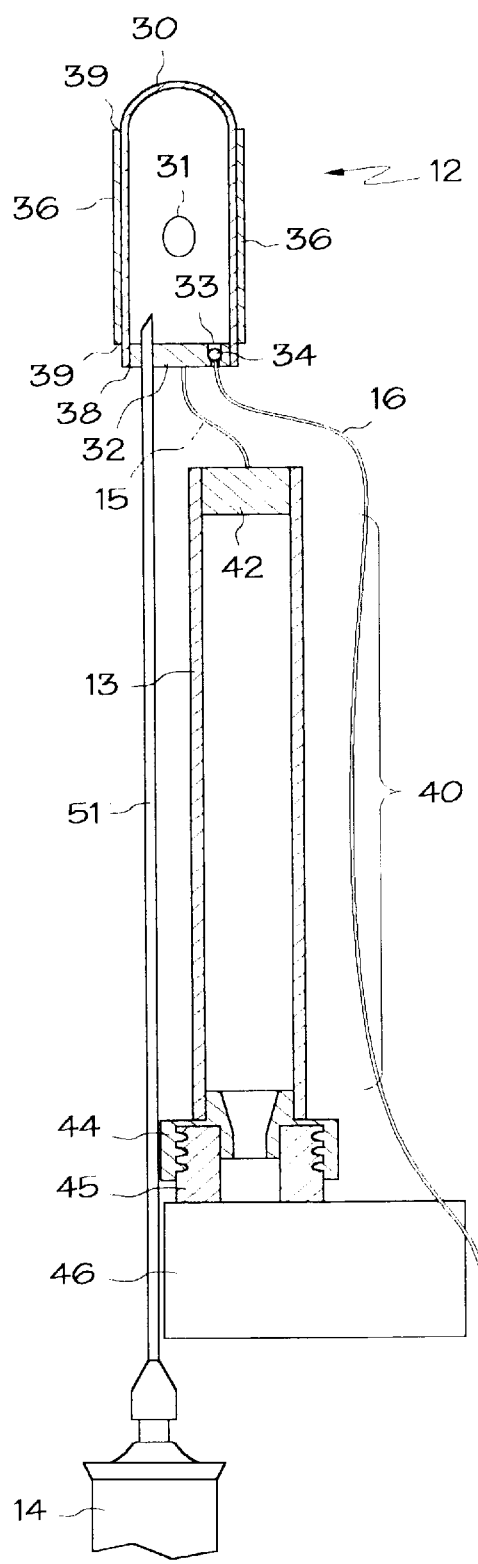
FIG. 4 is cross-sectional view of the pressure monitor probe of FIG. 1, wherein the balloon is depicted in its deflated state.

FIG. 4 is a cross-sectional view of the pressure monitor probe of the present invention, wherein distal portion 12 is depicted in its uninflated state. Distal portion 12 preferably comprises a hollow member 30 having a hemispherical distal end 37 and an open proximal end 38. Proximal end 38 provides access to the interior of hollow member 30. At least one aperture 31 is provided on the exterior surface of hollow member 30, and provides fluid communication between the interior and exterior of member 30.

The preferred inflatable feature of distal portion 12 may be provided by a variety of resilient materials, and may comprise, for example, a stretchable film extending over a portion of the external surface of distal portion 12. The inflatable feature may even be provided by a balloon which contained within member 30, such that upon inflation, the inflateed balloon protrudes away from member 30 through an opening and the like. In the presently preferred embodiment, however, distal portion 12 has a tubular balloon 36 secured about its circumference as shown. Balloon 36 may comprise, for example, a thin-walled section of polymeric (such as rubber) tubing which is stretched about hollow member 30. The upper and lower edges 39 of balloon 36 are secured to the exterior surface of member 30 as shown, such as by use of adhesives. In this manner, fluid expelled from the interior of member 30 through aperture 31 will inflate tubular balloon 36 in the manner depicted in FIG. 1.

In order to seal the interior of member 30, a plug 32 is secured within proximal end 38 of hollow member 30 as shown. Inflation of balloon 36 may be accomplished by means of a syringe, and thus needle shaft 51 of syringe 14 may be urged through plug 32 into the interior of hollow member 30. A 20 gauge spinal tap needle may be used for this purpose, and it is preferred that the syringe and balloon 36 be sized such that between about 15 and 20 CC of fluid is used to inflate balloon 36.

Although a passageway may be provided in plug 32 for entry of needle shaft 51, it is preferred that plug 32 act as a self-sealing septum. In other words, plug 32 is preferably made from a polymeric material through which needle shaft 51 may readily pass. Upon withdrawal of needle shaft 51, however, the passageway created by needle shaft 51 will close. Such materials are commonly employed, for example, in septums on medicinal vials, and may comprise, for example, various types of rubber. In this manner, needle shaft 51 may be urged through plug 32 until the tip of needle shaft 51 is within the interior of hollow member 30 as shown. A fluid, such as air or saline solution may then be urged through needle shaft 51 into the interior of hollow member 30 so as to inflate balloon 36.

Once balloon 36 has been sufficiently inflated, needle shaft 51 may be withdrawn from plug 32. Plug 32 will then self-seal so as to prevent escape of the inflation fluid. In this manner, once distal portion 12 is positioned within the patient's bladder and balloon 36 inflated, syringe 14 may be completely removed from the patient. As more fully described below, this allows catheter 13 to be the only structure remaining within the patient's urethra, thereby ensuring a more accurate determination of intraurethral pressure.

As best shown in FIG. 1, the inflation of balloon 36 prevents distal portion 12 from being withdrawn from the patient's bladder. Of course once the surgical procedures have been completed, a mechanism for removing distal portion 12 from the bladder must be provided. Although it is certainly possible that syringe 14 could be reinserted through the patient's urethra such that needle shaft 51 passes back through plug 32 into hollow member 30 for balloon deflation, urging needle shaft 51 through plug 32 may be difficult. Therefore, it is preferred that a separate deflation mechanism be provided. Numerous mechanisms for allowing deflation of distal portion 12 may be provided, and that described below is merely one example.

In one preferred embodiment, a deflation channel 33 is provided in plug 32 as shown in FIG. 4. Deflation channel 33 provides fluid communication between the interior and exterior of hollow member 30. Since plug 32 is self-sealing, however, deflation channel 33 should either be sufficiently large to prevent closure due to the inherent resiliency of plug 32 (i.e., the self-sealing feature), or alternatively, deflation channel 33 can be provided with rigid interior walls which prevent collapse of deflation channel 33. A stopper 34 (or any other type of removable plug) is positioned within deflation channel 33 as shown, and has a deflation string 16 (or other suitable member) attached thereto. Deflation string 16 extends out of deflation channel 33 and away from distal portion 12 as shown, such that when distal portion 12 is positioned within a patient's bladder, a portion of deflation string 16 will remain outside the patient's body. Deflation channel 33 is also preferably tapered as shown, so as to prevent expulsion of stopper 34 when balloon 36 has been inflated. When the surgical procedures have been completed, deflation string 16 may be pulled outwardly away from the patient's urethra, thereby pulling stopper 34 out of channel 33. When this occurs, balloon 36 will deflate, thereby allowing the probe to be removed from the patient.

As described previously, filament 15 may be used to attach distal portion 12 to catheter 13. Filament 15 may be molded directly into plug 32, or, alternatively, may be secured thereto by means of adhesives and the like. At its opposite end, filament 15 may be secured to catheter 13 in the same manner. Preferably, filament 15 is centered with respect to both plug 32 and the distal end of catheter 13.

As also shown in FIG. 4, catheter 13 essentially comprises an elongate, flexible, hollow tube, which is sealed at its distal end. For example, a distal end plug 42 may be positioned within catheter 13, as shown, in order to seal the distal end of catheter 13. Plug 42 may comprise any of a variety of materials, such as the same material used for plug 32 of distal portion 12. The purpose of distal end plug 42 is to seal the distal end of catheter 13, and to provide an attachment point for filament 15. The proximal end of catheter 13 has a fitting 44 secured thereto which allows catheter 13 to be attached to a pressure sensor or other pressure measuring apparatus. Fitting 44 may comprise, for example, a Leur lock fitting commonly employed in medical devices. A corresponding Luer lock fitting 45 on pressure monitor 46 allows the pressure monitor to be securely attached to fitting 44 of catheter 13, in fluid communication with the interior of catheter 13. The exterior of catheter 13 is also preferably provided with a series of graduations 49 (FIG. 1) which may be used to measure the length of the patient's urethra when the probe is inserted into the patient's urethra in the manner shown in FIG. 1.

Catheter 13 is preferably made from thin-walled, silicone tubing. Of course, other materials may be employed for catheter 13, with the only requirement being that the material be pressure responsive. In other words, the material employed for catheter 13 should be sufficiently resilient so that pressures exerted against the exterior of the urethra will result in a deformation of catheter 13. Deformation of the wall of catheter 13 will in turn increase the pressure of any fluid in the hollow interior of catheter 13, thereby providing a convenient means for measuring the amount of pressure applied to the wall of catheter 13. Since the fluid pressure within catheter 13 will correspond to the external pressure on the urethra (i.e., the pressure applied to the outer circumference of the urethra), the probe of the present invention provides a simple and accurate means for monitoring intraurethral pressure.

Catheter 13 may contain any of a variety of fluids, such as air or saline, so that deformation of catheter 13 caused by external pressure on the patient's urethra will cause a corresponding pressure increase in the fluid within catheter 13. In this manner, a conventional pressure monitoring assembly 46 may be used to monitor fluid pressure within catheter 13. It will be apparent that the region extending from distal end plug 42 to Leur lock fitting 44 comprises the pressure responsive region of catheter 13, and is identified as 40 in FIG. 5. By precisely controlling the length of filament 15, as well as a length of distal end plug 42, the pressure monitor probe of the present invention ensures that pressure responsive region 40 will be located in the desired, predetermined portion of the patient's urethra. Also of significance is that distal end plug 42, as well as distal portion 12, prevents bladder pressure from influencing the pressure measured by means of catheter 13, a problem associated with many prior art devices, since both prevent urine from escaping the bladder.

Pressure monitoring assembly 46 may comprise any of a variety of well-known devices. Preferably, pressure monitoring assembly 46 has a fitting 45 which corresponds to fitting 44 on catheter 13, thereby allowing pressure monitoring assembly 46 to be attached thereto. As mentioned previously, Leur lock fittings are preferably used for this purpose, however, the present invention is not so limited.

One preferred embodiment for pressure monitoring assembly 46 includes a pressure sensor in fluid communication with the interior of catheter 13. The pressure sensor is preferably of the type which provides a voltage response corresponding to fluid pressure within catheter 13. One such type of pressure sensor is that manufactured by SenSym Inc. of Milpitas, Calif., under the trade name SX15. The leads from this pressure sensor may be connected to appropriate circuitry well-known to those skilled in the art for providing a visual and/or audible indication of the pressure within catheter 13 (such as a small digital display). The entire pressure monitoring assembly may be provided in a small unit attached directly to catheter 13, as shown in FIG. 4. Alternatively, the pressure sensor may be attached to fitting 44 located at the proximal end of catheter 13, and thereafter wired to external circuitry positioned at a location more readily accessible and visible to the surgeon while the medical procedures are being performed. Of course various other types of well-known pressure monitoring apparatus or guages may be used in conjunction with the probe of the present invention.

The dimensions of the probe of the present invention should be selected to allow for accurate pressure readings within the urethra, while also allowing for ease of insertion. The diameter of distal portion 12, as well as catheter 13, should be selected so that they can both easily pass through the patient's urethra, and, particularly in the case of distal portion 12, should not be so large that removal is impeded. Catheter 13, however, should have a diameter sufficient to ensure that, once in place, it will completely fill the urethra without significant void spaces about its circumference. This ensures that accurate pressure readings can be obtained.

Figure 2:
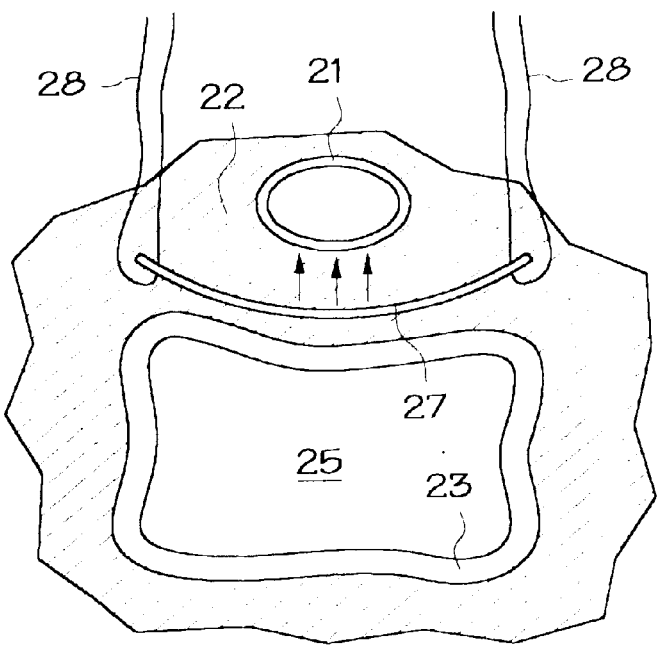
FIG. 2 is a cross-sectional view taken along the line 2—2 of FIG. 1 (with the pressure monitor probe omitted), wherein the patient's urethra has been elevated using a sling suspended by a pair of sutures.
Figure 3:
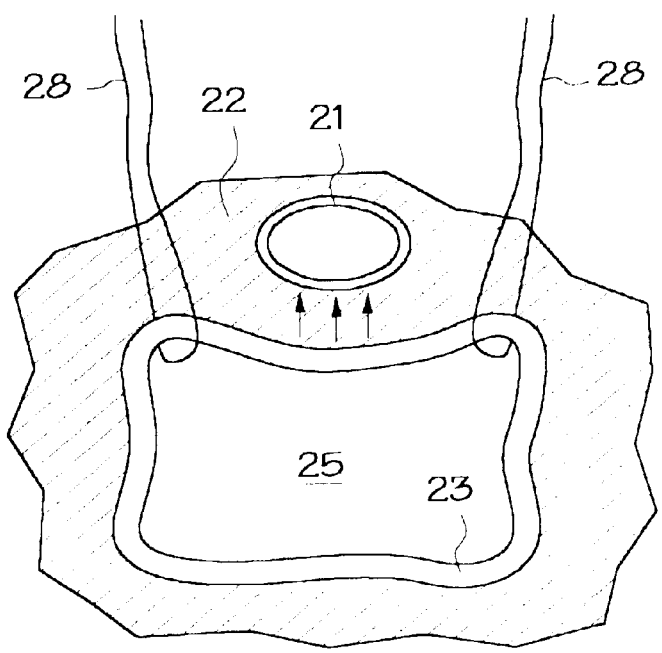
FIG. 3 is the same view as FIG. 2, wherein the patient's urethra has been elevated by means of a pair of sutures.

The method of using the probe of the present invention will generally not require the surgeon to deviate from his or her preferred procedure for correcting incontinence. In fact, one of the advantages of the probe of the present invention is that it can be readily employed in any incontinence procedure wherein the external pressure on the urethra is to be modified, whether by way of a sling which applies additional closure pressure to the urethra (FIG. 2), or a bladder neck suspension procedure (FIG. 3) wherein sutures or other appropriate support devices are employed to pull the periurethral tissue upwardly to provide additional external pressure on the urethra. In addition, the probe of the present invention can also be used during collagen injections to treat incontinence. In these procedures, collagen is injected into the tissue surrounding the urethra, and acts as a bulking agent. Since the injected collagen acts to increase external pressure on the urethra, the probe of the present invention can be used to ensure that the proper amount of collagen is injected. Too much collagen may prevent urination, while too little will not provide continence.

In order to facilitate insertion of the probe of the present invention, a rigid shaft is preferably positioned parallel and adjacent to the probe. Preferably, needle shaft 51 of inflation syringe 14 may conveniently be used for this purpose, and should therefore be inserted through plug 32 of distal portion 12 prior to insertion into the patient. In this manner, needle shaft 51 will improve the rigidity of this assembly, thereby facilitating insertion through the patient's urethra. Since catheter 13 should be very flexible and pliable, insertion of the probe without the use of needle shaft 51 may be difficult.

Figure 5:
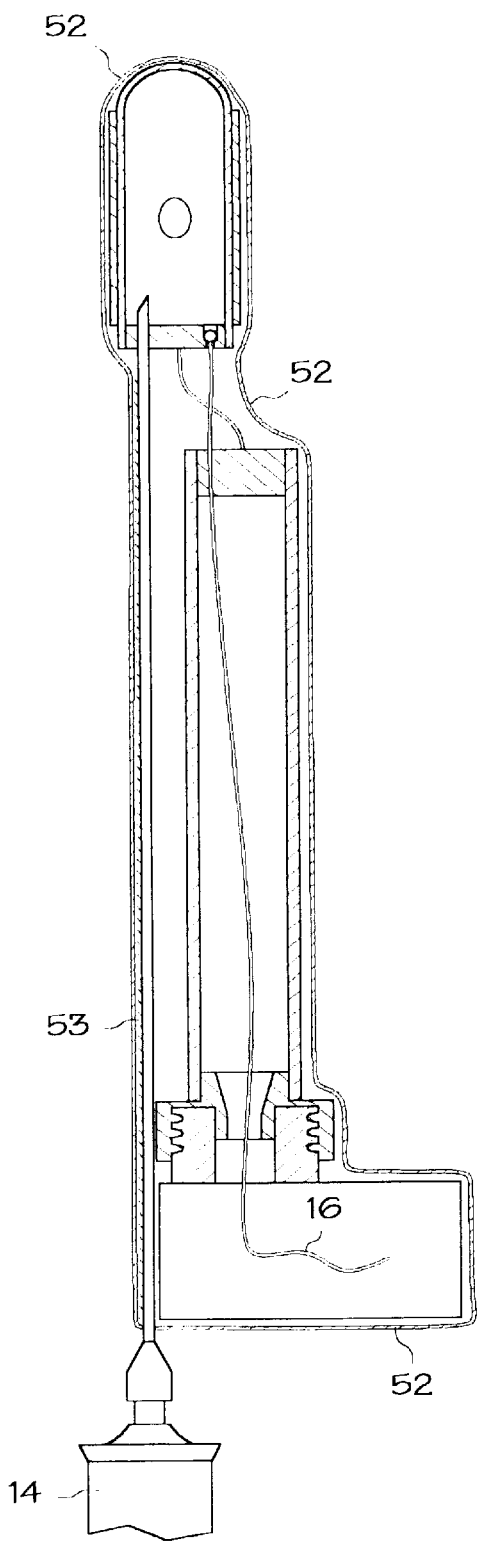
FIG. 5 is a cross-sectional view of a packaged pressure monitor probe of the present invention, wherein an inflation needle and syringe, as well as a pressure sensor are provided.

In order to further facilitate insertion, the entire assembly may be "shrink-wrapped" in the manner shown in FIG. 5. Thus, the entire assembly comprising distal portion 12, catheter 13, and a rigid shaft to facilitate insertion (such as needle shaft 51) is encased in a thin, polymeric film 52, with a portion of needle 51 protruding therefrom. More preferably, deflation string 16 and pressure monitor 46 are also encased by polymeric film 52, as shown. Furthermore, polymeric film 52 is preferably secured to needle shaft 51, such as by means of an adhesive 53 or even fused directly to needle shaft 51. A region of polymeric film 52 is also weakened, preferably by means of perforations, to allow removal of the film from the entire assembly. Thus, a line of perforation may extend about that portion of polymeric film 52 which covers the hemispherical end of hollow member 30 of distal portion 12. The line of perforation should be such that when needle shaft 51 is pulled away from distal portion 12, the line of perforation will separate in order to allow polymeric film 52 to be removed from the assembly along with needle shaft 51. When packaged in this manner, needle shaft 51 provides more than sufficient rigidity to allow for easy insertion of the probe into the patient's urethra. Polymeric film 52 may comprise any of a variety of materials commonly employed for shrink-wrapping.

As mentioned previously, filament 15 is preferably centered with respect to plug 32 of distal portion 12, as well as distal end plug 42 of catheter 13. Since filament 15 is highly flexible, when needle shaft 51 is extended through plug 32, catheter 13 will be deflected accordingly. Thus, as shown in FIGS. 4 and 5, catheter 13 is easily deflected out of alignment with distal portion 12 in order to accommodate needle shaft 51. Since the urethra is a pliable and flexible lumen, the assembly depicted in FIGS. 4 and 5 may be readily inserted through the patient's urethra towards the bladder without much difficulty. It should also be noted that the packaged assembly shown in FIG. 5 may be provided with or without an inflation syringe 14 attached thereto. In addition, the inflation channel 33 and the corresponding stopper 34 positioned therein may be omitted from the probe of the present invention. In this alternative embodiment, balloon deflation may be accomplished using the very same needle shaft 51 and inflation syringe 14 used to inflate the balloon. Therefore, it is contemplated that once the surgical procedures have been completed, pressure monitor 46 may be detached from catheter 13 to provide access to the interior of catheter 13. Thereafter, needle shaft 51 may be passed through the interior of catheter 13, through distal end plug 42, and thereafter through plug 32 of the distal portion 12 in order to deflate balloon 36.

Insertion of the probe of the present invention into the patient is relatively straight forward. The assembly depicted in FIG. 4 or FIG. 5 is inserted into the patient's urethra, with distal portion 12 leading. The probe is inserted the maximum possible distance, and balloon 36 is thereafter inflated by means of inflation syringe 14 attached to needle shaft 51. Once the appropriate amount of fluid has been injected into member 30, needle shaft 51 is withdrawn from the patient. Countertraction is then applied to the probe merely by pulling the probe outwardly away from the patient's urethra. This may be accomplished, for example, merely by grasping pressure monitor 46 and gently pulling outwardly. The result is that distal portion 12 will be seated within the patient's bladder at the UVJ, as shown in FIG. 1. It should be noted that the countertraction should be continually applied to the probe in order to anchor distal portion 12 in the desired location. In this manner, the surgeon is ensured that the pressure responsive region 40 of catheter 13 is positioned at the precise location which is spaced away from the UVJ. Preferably, filament 15, as well as distal end plug 42 of catheter 13, are both sized such that pressure responsive region 40 extends from a point about 0.2 to about 0.3 cm from the UVJ, to fitting 44 on catheter 13. This ensures that the pressure reading obtained will not be influenced by bladder pressure, and will take into account the external pressure applied along the entire length of the patient's urethra. In addition, the cylindrical nature of catheter 13 also provides a non-localized pressure responsive region 40. In other words, unlike some prior art pressure monitoring devices, the probe of the present invention can be used to measure intraurethral pressure around the entire circumference, as well as nearly the entire length of the urethra. The only portion of the urethra not bearing against pressure response region 40 is the small portion adjacent the UVJ whereat filament 15 and distal end plug 42 are located.

Once the pressure monitor probe of the present invention is positioned within the patient's urethra in the manner shown in FIG. 1, pressure monitor 46 will provide a measure of the external pressure applied against the urethra before surgical correction. This initial reading will provide the surgeon with an indication of the degree of correction which is needed, and may even be used to determine whether or not the patient is a candidate for the sling procedure shown in FIG. 2 or the less invasive bladder neck suspension procedure of FIG. 3. Therefore, the probe of the present invention may even be used for diagnostic purposes.

After the initial pressure reading has been obtained, the surgical procedure is then continued in the normal fashion. For example, the sling is positioned in the usual manner beneath the patient's urethra and thereafter suspended from an anatomical structure located above the urethra. Alternatively, when a bladder neck suspension is performed, the suspending sutures are positioned such that they extend between the periurethral tissue on either side of the urethra and the anatomical support structure located thereabove. While the surgeon is connecting the fixation device (e.g., the sling or sutures) to the anatomical structure located above the urethra, or injecting the bulking agent (e.g., collagen) around the urethra, the surgeon simultaneously monitors the pressure indicated by the pressure monitoring assembly. The surgeon may then adjust the tension in the sutures or sling, or continue injecting collagen, until the desired pressure reading is obtained. Once the desired pressure reading is obtained, the fixation device is secured in place or the injection of collagen is ceased. In this manner, the pressure monitor probe of the present invention provides a simple means for ensuring that the proper amount of external pressure is applied against the urethra. This will ensure that sufficient pressure to provide continence is provided, without applying so much pressure that the patient is unable to urinate.

The foregoing description of preferred embodiments is by no means exhaustive of the possible variations of the present invention, and has therefore been provided only for purposes of illustration and description. Modifications, variations and additions to the foregoing specific examples will be readily apparent to those skilled in the art in light of the teachings provided above, and are all well within the scope of the present invention. Thus, it is intended that the scope of the present invention be defined by the claims provided below, and not by any of the specific embodiments shown in the drawings and/or described above.

What we claim is:

1. A method of treating urinary incontinence in a patient, comprising:

(a) providing a pressure monitor probe, said probe comprising a catheter having a pressure responsive region and a distal portion, said pressure responsive region spaced a predetermined distance from said distal portion;

(b) inserting said pressure monitoring probe into the patient's urethra such that said distal portion is positioned at least partially within the patient's bladder adjacent the UVJ, thereby positioning said pressure responsive region within the urethra a predetermined distance from the UVJ; and (c) surgically modifying the pressure applied against the urethra while monitoring the pressure applied against the urethra using said probe.

2. The method of claim 1, wherein said step of surgically modifying the pressure applied against the urethra comprises elevating the patient's urethra.

3. The method of claim 2, wherein said step of elevating the patient's urethra comprises suspending a portion of the tissue adjacent the patient's urethra from an anatomical structure within the patient's body using a fixation device.

4. The method of claim 1, wherein said step of surgically modifying the pressure applied against the urethra comprises injecting a bulking agent adjacent to the patient's urethra.

5. The method of claim 1, wherein the interior of the catheter at said pressure responsive region is isolated from said distal portion.

6. The method of claim 5, wherein said distal portion is configured such that said distal portion prevents fluid communication between the bladder and the interior of the urethra.

7. The method of claim 5, wherein said catheter comprises an elongate, deformable tube, having distal and proximal ends, further comprising the step of providing a pressure monitor attached to said catheter, said pressure monitor configured so as to provide an indication of pressure applied to the exterior of said catheter.

8. The method of claim 7, wherein said catheter is hollow, and includes therein a fluid, and wherein said pressure monitor is responsive to the fluid pressure within said catheter.

9. The method of claim 5, further comprising the step of anchoring said distal portion within the patient's bladder.

10. The method of claim 9, wherein said distal portion is inflatable and said step of anchoring the distal portion within the bladder comprising inflating said distal portion.

11. The method of claim 10, wherein said distal portion comprises a hollow member having an aperture, and an inflatable portion positioned such that said aperture provides fluid communication between the interior of said hollow member and said inflatable portion, and wherein said inflation step comprises injecting a fluid into the interior of said hollow member so that said fluid is expelled through said aperture to inflate said inflatable portion.

12. The method of claim 11, further comprising the step of providing a fluid source, attaching said fluid source to said distal portion such that the fluid source is in fluid communication with the interior of said hollow member, and thereafter expelling fluid from said fluid source into the interior of said hollow member, thereby inflating said inflatable portion.

13. The method of claim 12, wherein said fluid source comprises a syringe having a needle attached thereto, and wherein said needle is attached to said distal portion by urging the tip of said needle into the interior of said distal portion.

14. An intraurethral pressure monitor probe, said probe comprising:
(a) a catheter having a pressure responsive region; and
(a) a distal portion spaced away from said pressure responsive region and configured such that the distal portion may be anchored within a patient's bladder;
wherein said probe is configured such when said distal portion is positioned at least partially within a patient's bladder adjacent to the UVJ and anchored in the bladder, said pressure responsive region of the catheter will be located in the urethra a predetermined distance from the UVJ.

15. The probe of claim 14, wherein said distal portion is inflatable.

16. The probe of claim 15, wherein said distal portion comprises a hollow member having an aperture, and an inflatable balloon positioned adjacent said aperture, and wherein said hollow member and said balloon are configured such that fluid expelled from the interior of said hollow member through said aperture will inflate said balloon.

17. The probe of claim 16, wherein said distal portion further comprises a deflation channel for selectively deflating said balloon.

18. The probe of claim 17, wherein said balloon comprises a polymeric tube which extends about the circumference of said hollow member.

19. The probe of claim 14, wherein said catheter comprises an elongate, deformable tube, having distal and proximal ends, and wherein said proximal end is attachable to a pressure sensor and said distal end is sealed.

20. The probe of claim 19, wherein said distal end of said catheter is attached to said distal portion.

21. The probe of claim 20, wherein said distal end of said catheter is attached to said distal portion by a flexible, non-stretchable connector.

22. The probe of claim 20, wherein said connector comprises a filament.

23. An intraurethral pressure monitoring assembly, comprising:
(a) an elongate pressure monitor probe;
(b) a rigid shaft extending parallel and adjacent to said probe; and
(c) a polymeric film enclosing at least a portion of said probe and said shaft;
said assembly configured such that at least a portion of said probe and said shaft may be inserted into a patient's urethra in order to monitor the pressure applied against the urethra.

24. The assembly of claim 23, wherein said film is secured to said shaft and has a weakened region configured such that when said shaft is pulled away from said probe, said film will separate at said weakened region and will be pulled away from said probe along with said shaft, thereby exposing said probe.

25. The assembly of claim 24, wherein said probe comprises a catheter having a pressure responsive region, and an inflatable distal portion spaced away from said pressure responsive region, and wherein said shaft comprises a needle and is attached to said distal portion such that fluid urged through said needle will inflate said distal portion.

26. The assembly of claim 23, further comprising a pressure monitor attached to one end of said probe.

27. The probe of claim 14, wherein said catheter is configured such when said distal portion is positioned at least partially within a patient's bladder adjacent to the UVJ and anchored in the bladder, said pressure responsive region of the catheter will be positioned within the urethra from the exterior entrance of the urethra to a point located said predetermined distance from the UVJ.

* * * * *